United States Patent [19]

Bajpai et al.

[11] 4,218,255

[45] Aug. 19, 1980

[54] POROUS CERAMIC CARRIERS FOR CONTROLLED RELEASE OF PROTEINS, POLYPEPTIDE HORMONES, AND OTHER SUBSTANCES WITHIN HUMAN AND/OR OTHER MAMILLIAN SPECIES AND METHOD

[75] Inventors: Praphulla K. Bajpai; George A. Graves, both of Dayton, Ohio

[73] Assignee: University of Dayton, Dayton, Ohio

[21] Appl. No.: 941,594

[22] Filed: Sep. 12, 1978

Related U.S. Application Data

[63] Continuation-in-part of Ser. No. 718,957, Aug. 30, 1976, abandoned.

[51] Int. Cl.$^2$ .................. A61M 7/00; C04B 33/24; C04B 35/44
[52] U.S. Cl. ..................................... 106/45; 106/73.3; 106/73.33; 106/73.4; 106/73.5; 128/260; 424/19
[58] Field of Search .................. 106/64, 104, 45, 73.4; 128/92 C, 260; 3/1.9; 424/16, 19

[56] References Cited

U.S. PATENT DOCUMENTS

| | | | |
|---|---|---|---|
| 2,021,520 | 11/1935 | Reichmann | 106/45 |
| 3,288,615 | 11/1966 | Estes et al. | 106/64 X |
| 3,919,723 | 11/1975 | Heimke et al. | 128/92 C |
| 4,135,935 | 1/1979 | Pfeil et al. | 106/45 |

FOREIGN PATENT DOCUMENTS

| | | | |
|---|---|---|---|
| 2163036 | 6/1973 | Fed. Rep. of Germany | 424/19 |
| 2331097 | 1/1975 | Fed. Rep. of Germany | 424/19 |

OTHER PUBLICATIONS

Graves, G. A. et al. "The Influence of Compositional Variations on Bone Ingrowth of Implanted Porous Calcium Aluminate Ceramics", J. Biomed. Mater Res. Symposium No. 6 (pp. 17-22) Jul. 1975.
Chem. Abstracts 76, (1972) item 30904j.
Chem. Abstracts 76, (1972) item 30905k.

*Primary Examiner*—Helen M. McCarthy
*Attorney, Agent, or Firm*—Anthony D. Cennamo

[57] ABSTRACT

The product and process of making an in-vivo body implant pharmaceutical carrier of a resorbable ceramic crystalline structure of interconnecting pores capable of the critical controlled time release of pharmaceutical preparations such as proteins, polypeptides, hormones, and other small molecular weight active materials. The ceramic is comprised of aluminum oxide ($Al_2O_3$), calcium oxide (CaO), and phosphorous pentoxide ($P_2O_5$) in a controlled weight percent mixture. In the process of making, the mixture is calcined. The calcined mixture is again ground and sieved through screens of two different mesh sizes to obtain desired sizes and mixed with a binder. This mixture is compressed and sintered at a predetermined temperature. The particle sizes of the sieved calcined compound and the sintering temperatures are interrelated to provide a ceramic of a desired pore size for the controlled release of the pharmaceutical.

8 Claims, No Drawings

POROUS CERAMIC CARRIERS FOR CONTROLLED RELEASE OF PROTEINS, POLYPEPTIDE HORMONES, AND OTHER SUBSTANCES WITHIN HUMAN AND/OR OTHER MAMILLIAN SPECIES AND METHOD

This application is a continuation-in-part of our co-pending application Ser. No. 718,957, now abandoned, filed Aug. 30, 1976 for, "Porous Ceramic Carrier for Controlled Release of Pharmaceutical."

BACKGROUND

The literature is replete with descriptions of long acting preparations of steroid hormones. Increased duration of activity has generally been achieved by chemical alteration of the parent molecule which, when injected intramuscularly, will form a depot. The injection provides biological effects spanning several weeks. Similar effects can be achieved by injecting aqueous microcrystalline suspensions of steroid hormones. More recent attempts have included steroids mixed with cholesterol or lipids and various steroidpermeable membranes.

An early attempt to obtain a longer acting steroid implant comprised mixing of stilbestrol, deoxycorticosterone acetate, testosterone propionate, progesterone, estrone or estradiol benzoate with cholesterol to provide 10, 25, 50, and 100% compositions. Each hormone and each composition was adsorbed differently. The addition of cholesterol, in general retarded adsorption in relation to pellets of pure hormone. However, others have reported an anti-fertility effect in mice with pellets containing 10 or 20% of 19-norprogesterone and 80% cholesterol.

Besides the prolonged action of these steroid preparations, the early studies indicated that except for progesterone these implants were well tolerated by the patients. The most important findings gained from the studies of these steroids was that a pellet of steroid will provide a pharmacological effect at a lower dose than was obtained by injecting an oil solution. The effect of a pellet may last several months.

It appears that two primary delivery systems are preferred by the prior art: steroid-lipid implants and polymer implants. The main difference in these two delivery systems is that permeation of steroids through polymer implants should be predictable. The geometry and total surface area exposed to body fluids remains constant, while with the steroid-lipid implant (other steroid pellets also), during the process of dissolution pattern becomes essentially level.

A number of methods of obtaining prolonged releases are already known. The drug may be enclosed in a capsule which will dissolve in the body after a certain amount of time. In microencapsulation, the drug is enclosed in a large number of very small membrane capsules. Others include tablets coated with lacquers to achieve delayed release; the drug suspended in water, oil, or buffer solution; the drug etherified or esterified to put it in a form in which it is difficult to reabsorb.

Absorption of the drug in carrier materials which can swell, such as gelatin, cellulose, or certain plastics also delays release. Drugs bonded by absorption to large surfaces, release slowly due to the low speed of resorption, such as with adsorbate innoculate or vaccine, a result of a mixture with aluminum hydroxide. If a powdered drug is compressed together with powdered plastics, a porous tablet will form in which the plastic material will partly cover the surface of the powdered drug and will delay its release.

CROSS-REFERENCE

Reference is made to the publication "The Influence of Compositional Variations on Bone Ingrowth of Implanted Porous Calcium Aluminate Ceramics" authored by George A. Graves (one of the inventors herein) F. R. Noyes, and G. R. Villanueva, J. Biomed. Mater. Res. Symposium, No. 6. pp. 17–22 (1975) The article is directed to a ceramic oxide composition as synthetic bone implants comprised of CaO, $Al_2O_3$, and $P_2O_5$. The process of making the controlled porous ceramic is not disclosed.

As can be appreciated a pharmaceutical release implant is many magnitudes more critical in structure than a bone implant. With a bone implant there would not be a real consequential effect if the implant were not 100% resorbable, whether fibers formed or other incidental matters. In a drug release, however, if the drug release is too slow or too fast for that specific drug the effects may be deleterious.

Accordingly, the aforementioned article is at best a discussion of several incomplete studies without proper conclusions.

It has now been found that the release of the pharmaceutical in the in-vivo body is directly related to the resorption of the ceramic; and which resorption is directly related to the pore size of the ceramic containing the drug.

SUMMARY OF INVENTION

The invention is for a porous resorbable ceramic carrier capable of controlling the critical release of pharmaceuticals such as proteins, polypeptides, hormones, and other large molecular weight materials within the physiological environment, that is, the living body. The drug-containing ceramic is intended to be implanted subcutaneously or intermuscularly in the body.

The resorbable carrier is composed of a ceramic material with interconnecting pores fabricated into a hollow-cylinder for encapsulation of the pharmaceutical. The initial ceramic composition and fabrication parameters particularly the particle sizes temperature and the sintering determine the crystallographic phases and final pore size of the ceramic which controls the rate of drug release and ceramic resorption in-vivo. That is the rate of delivery and lifetime of the ceramic carrier is determined by its microstructure and composition. In turn, the crystallographic structure and pore size can be controlled in its process of making to be adapted to the intrinsic properties of a specific drug and the requirement of the body.

The carrier drug composition comprised the group of oxides: aluminum oxide ($Al_2O_3$), calcium oxide (CaO), and phosphorus pentoxide ($P_2O_5$), with minor additions of magnesium oxide ($M_gO$), zinc oxide (ZnO), silicon dioxide ($SiO_2$), zirconium dioxide ($ZrO_2$), and titanium dioxide ($TiO_2$). The heavier metal oxides are to be excluded. The total impurity content is to be less than 1 weight percent.

The three primary components in a 100 weight percent mixture are calcined at a temperature and time for an improved crystallographic structure. The calcined mixture is again ground into powder and sieved through screens of two different mesh sizes to yield a distribution of particle sizes in a range between said two mesh sizes. The powder is mixed with a binder and is compressed and sintered at a predetermined temperature interrelated to the two particle sizes to provide a ceramic of a desired pore size and crystallographic structure. Specific particle sizes with specific temperatures have been determined for a controlled pore size.

OBJECTS

It is a principal object of the present invention to provide a new and improved implant in-vivo pharmaceutical, wherein the pharmaceutical is encapsulated in a carrier that is resorbable in a controlled manner and completely acceptable to the body without toxic effects.

It is a further object of the present invention to provide a new and different process for the making of an in-vivo implant resorbable over a controlled time period.

DETAILED DESCRIPTION OF INVENTION

The drug implant composition of the present invention is a ceramic composed of at least two identifiable crystallographic phases. The ceramic material is compressed into hollow cylinders or other shapes such as a pharmaceutical carrier. The carrier comprises a microstructure that allows for the release of the pharmaceuticals such as hormones, proteins, and other chemical substances. The released material flows or diffuses from the hollow center through the pore structure of the ceramic carrier to the exterior surface and into the physiological fluids of the body. The rate of release of the drug, chemical, etc., is therefore, partially dependent on the microstructure of the ceramic carrier. The ceramic microstructure in turn is varied by the chemical composition processing parameters such as particle size of dry powder, and temperature cycle during sintering, as well as other ceramic engineering techniques.

The ceramics' main crystallographic phase is composed of oxides of the group: aluminum oxide ($Al_2O_3$), calcium oxide (CaO), and phosphorous pentoxide ($P_2O_5$) with minor additions of magnesium oxide (MgO), zinc oxide (ZnO), and dioxides of the groups: silicon dioxide ($SiO_2$), zirconium dioxide ($ZrO_2$), and titanium dioxide ($TiO_2$), with impurities less than 1 percent by weight.

The heavy metal oxides are to be excluded. The heavy metals such as lead, cobalt, chromium and iron oxide were found unsuitable since they are known to disassociate and accumulate in the skeletal structure and cause untoward effects after a period of time.

In an early process the steps utilized in making the resorbable crystalline ceramic were based on a 100% mixture of (CaO) and ($Al_2O_3$). That is 42 weight percent of (CaO) and 58 weight percent of ($Al_2O_3$). After preparation there was added a 10-25 weight percent of phosphorous pentoxide ($P_2O_5$).

A much improved process in the making of the resorbable crystalline ceramic has now been found to comprise a 100% mixture of (CaO), ($Al_2O_3$), and ($P_2O_5$). More specifically one mixture comprised of 50 weight percent of ($Al_2O_3$), 37.7 weight percent of (CaO), and 12.3% of ($P_2O_5$).

The powdered material was compressed under pressure and then calcined. The calcining temperature was 2400° F. for a period of 12 hours.

The calcined composition was again powdered by grinding and controlled in size by passing the mixture through mesh screens. For the mixture calcined at 2400° F. the powder was −250 mesh and +325 mesh.

The mixture was formed into a green shape by mixing the same with polyvinyl alcohol and compressing the mixture in a die. The pressure applied was 20,000 psi.

The green shaped composition is then sintered at a predetermined temperature and time. Specifically it has been found that the pore size of the ensuing product is directly related to the aforementioned particle sizes and the temperature of the sintering. It has been found that the −325 and +400 mesh particle sizes would be sintered at 2300° F., the −250 and +325 mesh particle sizes would be sintered at 2400° F., whereas the −200 and +250 mesh particle sizes would be sintered at 2600° F. These particle sizes/sintering temperatures yielded the desired pore sizes for a particular drug delivery.

As aforesaid the composition comprised a 100% mixture of ($Al_2O_3$), (CaO), and ($P_2O_5$) whereas in our earlier studies the ($P_2O_5$) was later added. The 100% mixture was found to provide a more homogeneous mixture and resulted in a better crystallographic phases. In this way there would be no concentrated areas of ($P_2O_5$); thereby providing a more uniform resorbtion.

Again, although not particularly significant in drug delivery, the 100% mixture rsulted in a ceramic having a higher mechanical strength.

The calcining procedure was changed also from our earlier findings. The higher heat at a shorter time period was found to give a different crystallographic structure from that previously obtained.

The sintering rate and temperature as well as other ceramic processing factors can be varied to vary the resorption rate of the composition. The resorption rate is directly related to the pore size and composition of the ceramic. Accordingly, varying the resorption rate does vary the pore size and composition. The correct microstructure must be determined for the ceramic for each drug used.

As mentioned above specific pore sizes for particular resorption rates has been found and reproduced with specific particle sizes and sintering temperatures.

Again screening the mixture in a controlled size screen, rather than a broad range of sizes, yields particles having a more finite size. Accordingly, varying of the size in altering the pore size of the end product is more finitely controlled. Significantly, this in turn tends to eliminate defects in the ceramics.

The continuous delivery of a drug at a controlled rate, for long periods of time is accomplished without the need for percutaneous leads. The drug-containing ceramic is implanted subcutaneously in the body with minor surgery. The success of the implant is dependent upon the ability of the ceramic to resorb within the body due to its chemical composition and microstructure. The composition, processing parameters, and final ceramic microstructure are considered for each drug and the physiological system receiving the drug.

The resorption of the implant ceramic allows for the implanting of a pharmaceutical delivery system that can last for an identifiable length of time before dissolving (resorbing) in-vivo and therefore does not have to be removed. This eliminates the need for medication requiring daily injections attendant with its physical trauma to the physiological system that is accumulative, and the psychological problems. Additionally, the resorbable implant eliminates the side effects that commonly accompany transcutaneous injections on a daily (or more frequent) basis.

An immediate clinical medical application for the implant resorbable ceramic is in the delivery of a continuous dosage of insulin to diabetics. In practice, the above described crystalline ceramic, tubular in form and having insulin in the cavity therein, was implanted in an animal, pancreatomised by streptozocin and alloxan treatment. The blood sugar levels were tested continuously and were maintained at the pre-streptozocin-alloxan treatment levels for a period of at least one month. The ability to supply insulin for periods of six to twelve months with one implant is now within the state of the art. Other expected uses of the implant ceramic is in the continuous delivery, at constant rate, of polypeptide hormones, proteins, and other large molecular weight substances that are required on a continuous basis.

The resorption is accomplished by the body fluids seeping into the pores and dissolving the material to release the insulin. Functionally, upon resorption of the implant ceramic the pore size of the implant increases thereby gradually increasing the release of the pharmaceutical. As the pharmaceutical supply decreases the pore size increases thereby maintaining a steady flow of pharmaceutical into the body.

Although only a specific and certain embodiment of the invention has been shown and described, it must be appreciated that modifications may be had thereto without departing from the true spirit and scope of the invention.

We claim:

1. The process of forming an in-vivo implant which is a porous, resorbable ceramic material having interconnected pores and suitable for the prolonged release of a pharmaceutical comprising:

powdering and mixing together oxides comprising by weight about 38% CaO, 50% $Al_2O_3$ and 12% $P_2O_5$, and with impurities less than 1%, and compressing said mixture, calcining said mixture at approximately 2400° F. for 12 hours to yield a crystallographic structured ceramic of at least two phases, powdering said calcined mixture and sieving the same through screens of two different mesh sizes to obtain particles ranging from a size that passes through 200 mesh (−200) and is retained on 400 mesh (+400), mixing with a binder and thereafter compressing said powdered mixture at a pressure of about 20,000 psi, and then, sintering said mixture for a time and temperature related to the average particle size.

2. The process of claim 1 wherein the oxides include minor additions of MgO, ZnO, $SiO_2$, $ZrO_2$, and $TiO_2$.

3. The process of claim 1 wherein said sieving was with 250 and 300 mesh screens and said sintering temperature was 2400° F., to yield a crystallographic structured ceramic having a given pore size.

4. The process of claim 1 wherein said sieving was with 200 and 250 mesh screens and said sintering temperature was 2600° F., to yield a crystallographic structured ceramic having a given pore size.

5. The process of claim 1 wherein said sieving was with 325 and 400 mesh screens and said sintering temperature was 2300° F., to yield a crystallographic structured ceramic having a given pore size.

6. The product of the process of claim 3.

7. The product of the process of claim 4.

8. The product of the process of claim 5.

* * * * *